US00PP35249P2

(12) United States Plant Patent
Koppe

(10) Patent No.: US PP35,249 P2
(45) Date of Patent: Jul. 4, 2023

(54) ***BEGONIA* PLANT NAMED 'KROUTBA01'**

(50) Latin Name: ***Begonia boliviensis* X *Begonia* x *tuberhybrida***
Varietal Denomination: KROUTBA01

(71) Applicant: KOPPE ROYALTY B.V., Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 17/990,381

(22) Filed: Nov. 18, 2022

(51) Int. Cl.
*A01H 5/02* (2018.01)
*A01H 6/18* (2018.01)

(52) U.S. Cl.
USPC ..... Plt./343
CPC ..... *A01H 6/185* (2018.05); *A01H 6/18* (2018.05)

(58) Field of Classification Search
USPC ..... Plt./343
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Begonia* plant named 'KROUTBA01', characterized by its upright to spreading and mounded plant habit; moderately vigorous growth habit; moderately freely branching habit; dark green-colored leaves; single-type white-colored flowers with pink-colored margins that are positioned above and beyond the foliar plane; and continuous flowering throughout the summer.

1 Drawing Sheet

Figure 1:
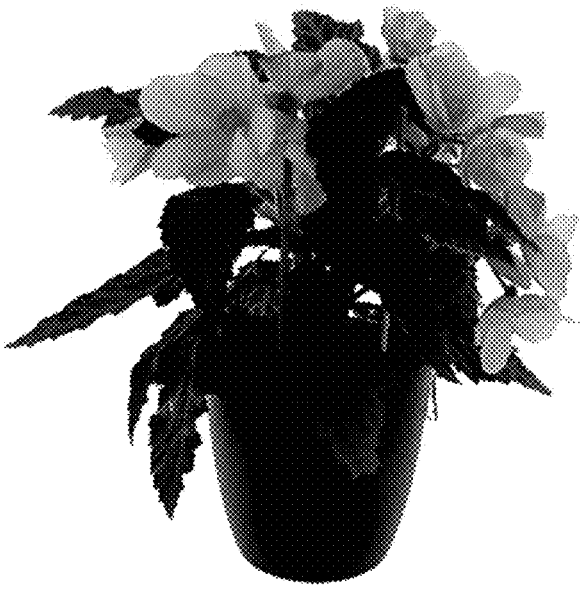

Botanical designation: *Begonia boliviensis* X *Begonia* x *tuberhybrida*.
Cultivar denomination: 'KROUTBA01'.

STATEMENT REGARDING PRIOR DISCLOSURES BY THE INVENTOR & APPLICANT/ASSIGNEE

An European Community Plant Breeder's Rights application for the instant plant was filed by the Applicant/Assignee, Koppe Royalty B.V. of Putten, The Netherlands on Oct. 6, 2022, application number 2022/2224. Foreign priority is not claimed to this application.

BACKGROUND OF THE INVENTION

The present invention relates to a new and distinct cultivar of *Begonia* plant, botanically known as *Begonia boliviensis* X *Begonia* x *tuberhybrida* and hereinafter referred to by the name 'KROUTBA01'.

The new *Begonia* plant is a product of a planned breeding program conducted by the Inventor in Ermelo, The Netherlands. The objective of the breeding program is to create new *Begonia* plants with uniform plant habit and numerous attractive flowers.

The new *Begonia* plant originated from a cross-pollination made by the Inventor in Ermelo, The Netherlands in December, 2016 of *Begonia boliviensis* 'Million Kisses Elegance', not patented, as the female, or seed, parent with a proprietary selection of *Begonia* x *tuberhybrida* identified as code number KV14K1807-009, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in June, 2017.

Asexual reproduction of the new *Begonia* plant by terminal vegetative cuttings taken in a controlled greenhouse environment in Ermelo, The Netherlands since March, 2018 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KROUTBA01'. These characteristics in combination distinguish 'KROUTBA01' as a new and distinct *Begonia* plant:

1. Upright to spreading and mounded plant habit.
2. Moderately vigorous growth habit.
3. Moderately freely branching habit.
4. Dark green-colored leaves.
5. Single-type white-colored flowers with pink-colored margins that are positioned above and beyond the foliar plane.
6. Continuous flowering throughout the summer.

Plants of the new *Begonia* differ primarily from plants of the female parent, 'Million Kisses Elegance', in the following characteristics:

1. Plants of the new *Begonia* are more freely flowering than plants of 'Million Kisses Elegance'.
2. Leaves of plants of the new *Begonia* are darker green in color than leaves of plants of 'Million Kisses Elegance'.

3. Plants of the new *Begonia* have larger and more open flowers than plants of 'Million Kisses Elegance'.

Plants of the new *Begonia* differ primarily from plants of the male parent selection in the following characteristics:

1. Plants of the new *Begonia* are larger than plants of the male parent selection.
2. Plants of the new *Begonia* and the male parent selection differ in flower color as plants of the new *Begonia* have white-colored flowers with pink-colored margins whereas plants of the male parent selection have solid pink-colored flowers.

Plants of the new *Begonia* can be compared to plants of *Begonia boliviensis* X *Begonia* x *tuberhybrida* 'KROUTYE01', disclosed in U. S. Plant Pat. No. 32,637. In side-by-side comparisons conducted in Ermelo, The Netherlands, plants of the new *Begonia* differed primarily from plants of 'KROUTYE01' in flower color as plants of the new *Begonia* have white-colored flowers with pink-colored margins whereas plants of 'KROUTYE01' have light yellow-colored flowers. In addition, plants of the new *Begonia* have darker green-colored leaves.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph at the top of the sheet (FIG. 1) is a side perspective view of a typical plant of 'KROUTBA01' grown in a container.

Figure 2:
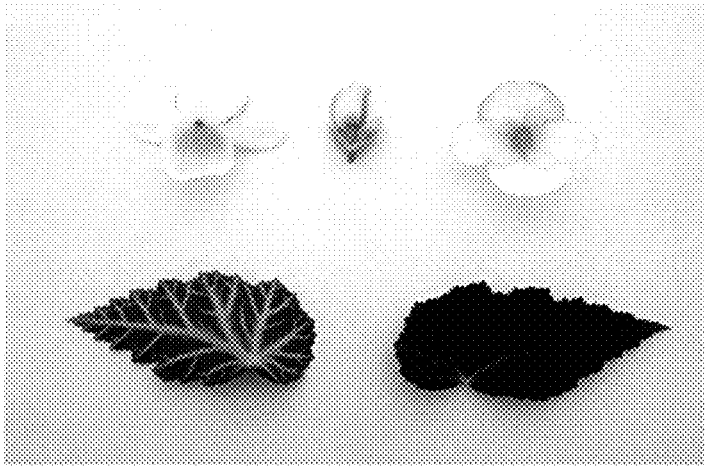

The photograph at the bottom of the sheet (FIG. 2) is a close up view of typical flowers and leaves of 'KROUTBA01'.

DETAILED BOTANICAL DESCRIPTION

The aforementioned photographs and following observations and measurements describe plants grown during the late summer and early autumn in 12-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were six weeks old when the photographs and description were taken. In the following description, color references are made to The Royal Horticultural Society Colour Chart, 2015 Edition, except were general terms of ordinary dictionary significance are used.

Botanical classification: *Begonia boliviensis* X *Begonia* x *tuberhybrida* 'KROUTBA01'.

Parentage:

*Female, or seed, parent.*—*Begonia* x *tuberhybrida* 'Million Kisses Elegance', not patented.

*Male, or pollen, parent.*—Proprietary selection of *Begonia* x *tuberhybrida* identified as code number KV14K1807-009, not patented.

Propagation:

*Type.*—By terminal vegetative cuttings.

*Time to initiate roots, summer and winter.*—About 20 days at temperatures about 20° C.

*Time to produce a rooted young plant, summer and winter.*—About five weeks at temperatures about 20° C.

*Root description.*—Fine, fibrous; typically white to orange brown in color, actual color of the roots is dependent on substrate composition, water quality, fertilizer type and formulation, substrate temperature and physiological age of roots.

*Rooting habit.*—Freely branching; medium density; plants of the new *Begonia* have not been observed to form tubers to date.

Plant description:

*Plant habit and form.*—Upright to spreading and mounded plant habit; globular in overall plant shape.

*Growth habit.*—Moderately vigorous growth habit and moderate growth rate; suitable for 9-cm and larger containers; under optimal environmental and cultural conditions, usually about six weeks are required to produce proportional 12-cm potted plants from rooted cuttings.

*Branching habit.*—Moderately freely branching habit, about three basal branches each with about one secondary branch developing per plant; dense and bushy plant habit.

*Plant height, soil level to top of foliar plane.*—About 19.4 cm.

*Plant height, soil level to top of floral plane.*—About 19.9 cm.

*Plant width.*—About 34.8 cm.

*Lateral branches.*—Length: About 6.5 cm. Diameter: About 8 mm to 9 mm. Internode length: About 1.4 cm. Aspect: Erect to about 30° from vertical. Strength: Flexible, bending with the weight of the flowers. Texture and luster: Moderately to densely pubescent; slightly velvety; slightly glossy. Color, developing: Close to 148A to darker than 148A. Color, developed: Darker than a blend of 148A and 152A; sun-exposed surfaces are tinged with close to N199A.

*Leaves.*—Arrangement: Alternate; simple. Length: About 16.1 cm. Width: About 7.2 cm. Shape: Narrowly ovate. Apex: Acuminate. Base: Broad unequal truncate to shallowly oblique, lobes free. Margin: Crenate to dentate; moderately undulate; unlobed. Texture and luster, upper surface: Moderately pubescent; not rugose; velvety; matte to slightly glossy. Texture and luster, lower surface: Moderately pubescent; not rugose; velvety; slightly glossy. Venation pattern: Pinnate. Color: Developing leaves, upper surface: Close to 200B and 200C; venation, close to 151B. Developing leaves, lower surface: Close to 187B; venation, close to 146D. Fully expanded leaves, upper surface: Close to a blend of 147A and N189A, tinged with close to 203A; areas adjacent to venation, close to a blend of 137A and 141A; venation, close to 151A. Fully expanded leaves, lower surface: Close to 185A; areas adjacent to venation, close to 147C; venation, close to 152A. Petioles: Length: About 4.4 cm. Diameter: About 4.5 mm. Texture and luster, upper and lower surfaces: Moderately pubescent; moderately glossy. Strength: Low, flexible. Color, upper surface: Close to N199C; distally, close to 185A. Color, lower surface: Close to a blend of 199A and N199C. Stipules: Quantity and appearance: Two leafy stipules positioned at base of the leaf. Length: About 9 mm. Width: About 7 mm. Shape: Broadly ovate. Apex: Broadly acute. Base: Broadly cuneate. Margins: Ciliate. Color, upper and lower surfaces: Close to 145D; venation, close to 145B; ciliate margins, close to 157D.

Flower description:

*Flower form and flowering habit*.—Single female and male rotate flowers arranged in axillary cymes; typically about three flowers per cyme, numerous cymes in flower simultaneously and at one time, about 27 flowers per plant; about 66.7% of the flowers are male; flowers face upright to outwardly and are positioned above and beyond the foliar plane.

*Natural flowering season*.—Plants flower continuously from the spring into the autumn in The Netherlands.

*Flower longevity*.—Individual flowers last about ten days on the plant; flowers not persistent.

*Fragrance*.—None detected.

*Inflorescence height (including peduncle)*.—About 13.6 cm.

*Inflorescence diameter*.—About 12.9 cm.

*Flower buds, female flowers*.—Length: About 2.7 cm. Diameter: About 1.3 cm. Shape: Ovate. Texture and luster: Smooth, glabrous; velvety; matte. Color: Close to 145C tinged with close to 50D; wings, close to 145A.

*Flower buds, male flowers*.—Length: About 2.2 cm. Diameter: Ranging from about 1 cm to 2.6 cm. Shape: Reniform to broadly obovate, flattened. Texture and luster: Smooth, glabrous; velvety; matte. Color: Close to 51D; towards the base, close to 145C; venation, close to 146D.

*Female flowers*.—Diameter: About 5.8 cm by 5.8 cm. Depth (including ovary): About 4 cm. Shape: Rotate, single. Tepals: Quantity and arrangement: About five arranged in a single whorl. Length: About 3.9 cm. Width: About 3 cm. Shape: Broadly ovate to broadly elliptic to obovate. Apex: Acute to obtuse, occasionally retuse. Base: Cuneate. Margin: Entire; distally, occasionally dentate; not undulate. Texture and luster, upper surface: Smooth, glabrous; velvety; matte. Texture and luster, lower surface: Smooth, glabrous; moderately velvety; matte. Color: When opening, upper surface: Close to N155B; towards the base, close to 157A; narrow edges, close to 51C. When opening, lower surface: Close to NN155D; towards the base, close to 157A; towards the margins and apex, close to 52B and 52C. Fully opened, upper surface: Close to NN155D; narrow edges, close to 52C; venation, close to NN155D; color does not change with subsequent development. Fully opened, lower surface: Close to NN155D; towards the margins and apex, close to 55A to 55C; venation, close to N155A; color does not change with subsequent development. Tepaloids: None observed on female flowers.

*Male flowers*.—Diameter: About 7.4 cm by 7.4 cm. Depth (including ovary): About 3.9 cm. Shape: Rotate, single. Tepals: Quantity and arrangement: About two, opposite. Length: About 4.8 cm. Width: About 4.4 cm. Shape: Broadly obovate. Apex: Acute to obtuse, occasionally retuse. Base: Cuneate. Margin: Entire; distally, occasionally dentate; not undulate. Texture and luster, upper surface: Smooth, glabrous; velvety; matte. Texture and luster, lower surface: Smooth, glabrous; moderately velvety; matte. Color: When opening, upper surface: Close to N155B; towards the base, close to 157A; narrow edges, close to 51C. When opening, lower surface: Close to NN155D; towards the base, close to 157A; towards the margins and apex, close to 52B and 52C. Fully opened, upper surface: Close to NN155D; narrow edges, close to 52C; venation, close to NN155D; color does not change with subsequent development. Fully opened, lower surface: Close to NN155D; towards the margins and apex, close to 55A to 55C; venation, close to N155A; color does not change with subsequent development. Tepaloids: Quantity and arrangement: About six to nine arranged in two whorls. Length: About 2.1 cm to 5 cm. Width: About 0.7 cm to 2.5 cm. Shape: Obovate to narrowly obovate and oblong. Apex: Obtuse. Base: Acuminate to cuneate. Margin: Entire, not undulate. Texture and luster, upper surface: Smooth, glabrous; velvety; matte. Texture and luster, lower surface: Smooth, glabrous; moderately velvety; matte. Color: When opening, upper surface: Close to N155B; towards the base, close to 157C; narrow edges, close to 51C. When opening, lower surface: Close to NN155D; towards the base, close to 157B; towards the margins and apex, close to 55B and 55C. Fully opened, upper surface: Close to NN155D; narrow edges, close to 52C; towards the base, close to 10A; venation, close to NN155D; color does not change with subsequent development. Fully opened, lower surface: Close to NN155D; towards the margins and apex, close to 55A to 55C; towards the base, close to 154D; venation, close to N155A; color does not change with subsequent development.

*Flower bracts*.—Quantity and arrangement: Two positioned at the top of the peduncle. Length: About 9 mm. Width: About 1.5 cm. Shape: Reniform. Apex: Obtuse and finely serrate. Base: Broadly cuneate. Margin: Finely serrate. Texture and luster, upper and lower surfaces: Smooth, glabrous; matte. Color, upper and lower surfaces: Close to 145B.

*Peduncles*.—Length: About 6.9 cm. Diameter: About 3.5 mm by 4 mm. Angle: About 27.5° from lateral branch axis. Strength: Flexible, bending with the weight of the flowers. Texture and luster: Smooth, glabrous; moderately glossy. Color: Close to N199A tinged with close to 185B.

*Pedicels*.—Length: About 3 cm. Diameter: About 3 mm. Angle: Primary flowers, erect and secondary flowers, about 40° from peduncle axis. Strength: Flexible, bending with the weight of the flowers. Texture and luster: Sparsely pubescent; moderately glossy. Color, upper and lower surfaces: Close to 146D, variably tinged with close to 178C.

*Reproductive organs*.—Stamens (present on male flowers only): Quantity per flower: About 50. Filament length: About 4 mm. Filament color: Close to 17D. Anther shape: Elliptic. Anther size: About 1.5 mm by 2 mm. Anther color: Close to 17A. Pollen amount: Moderate. Pollen color: Close to 11C. Pistils (present on female flowers only): Quantity per flower: About three. Pistil length: About 8 mm. Style length: About 5 mm. Style color: Close to 11C. Stigma diameter: About 7 mm. Stigma color: Close to 9B. Ovary color: Close to 144C; distally, close to 51B.

*Seeds and fruits*.—To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KROUTBA01' as illustrated and described.

* * * * *